United States Patent [19]

Stahly et al.

[11] Patent Number: 4,990,658
[45] Date of Patent: Feb. 5, 1991

[54] PROCESS FOR PREPARING IBUPROFEN AND ITS ALKYL ESTERS

[75] Inventors: Barbara C. Stahly; Ronny W. Lin, both of Baton Rouge; E. E. Atkinson, Jr., Greenwell Springs, all of La.

[73] Assignee: Ethyl Corporation, Richmond, Va.

[21] Appl. No.: 451,563

[22] Filed: Dec. 18, 1989

[51] Int. Cl.$^5$ ............................................. C07C 51/14
[52] U.S. Cl. ..................................... 562/406; 560/105
[58] Field of Search ......................... 562/406; 560/105

[56] References Cited

U.S. PATENT DOCUMENTS

| | | | |
|---|---|---|---|
| 4,034,004 | 7/1977 | Cassar et al. | 562/406 |
| 4,439,618 | 3/1984 | Cometti et al. | 560/56 |
| 4,536,595 | 8/1985 | Gardano et al. | 562/406 |
| 4,537,970 | 8/1985 | Foa et al. | 546/319 |
| 4,654,436 | 3/1987 | Lane et al. | 562/406 |
| 4,713,484 | 12/1987 | Epstein | 562/406 |

FOREIGN PATENT DOCUMENTS 89303995.8 10/1989 European Pat. Off. .
53-101329 9/1978 Japan .

*Primary Examiner*—Paul J. Killos
*Attorney, Agent, or Firm*—Richard J. Hammond

[57] ABSTRACT

A new process for preparing ibuprofen or its alkyl esters is provided. A 1-halo-1-(4-isobutylphenyl)ethane is reacted with carbon monoxide in the presence of water or an alcohol at a temperature between about 10° C. and about 200° C. An excess of several moles of water or alcohol is preferred. An acid such as hydrochloric acid may also be added. As catalyst, a palladium compound and at least one acid-stable ligand are present; however an excess of ligand over palladium is advantageous.

41 Claims, No Drawings

PROCESS FOR PREPARING IBUPROFEN AND ITS ALKYL ESTERS

TECHNICAL FIELD

This invention relates to a process for preparing 2-(4-isobutylphenyl)propionic acid, a pharmaceutical which is better known as ibuprofen, or an ester thereof.

BACKGROUND

There are many known processes for preparing ibuprofen, but there is still a need for a more economical process. Among the known processes for preparing 2-(4-isobutylphenyl)propionic acid or esters thereof is that of Shimizu et al. (U.S. 4,694,100, issued Sep., 1987), who teach the reaction of p-isobutylstyrene with carbon monoxide and water or alcohol in the presence of a complex carbonylation catalyst. They also teach the alternative reaction of the p-isobutylstyrene with carbon monoxide and hydrogen in the presence of a metal complex carbonyl catalyst to produce 2-(4-isobutylphenyl)propionaldehyde, which is then oxidized to produce the desired product. They teach the preparation of their starting material by the reaction of isobutylbenzene with acetaldehyde in the presence of sulfuric acid, producing 1,1-bis(4-isobutylphenyl)ethane, which is then catalytically cracked to produce p-isobutylstyrene and isobutylbenzene.

Another process for preparing ibuprofen is that of European Patent Application 284,310 (Hoechst Celanese, published Sep., 1988), which teaches that ibuprofen can be prepared by carbonylating 1-(4-isobutylphenyl)ethanol with carbon monoxide in an acidic aqueous medium and in the presence of a palladium compound/phosphine complex and dissociated hydrogen and halide ions, which are preferably derived from a hydrogen halide. This process has the disadvantage of starting with 1-(4-isobutylphenyl)ethanol, a compound which is not economical to make by known processes.

Gardano et al. (U.S. 4,536,595, issued Aug., 1985) teach the preparation of alkaline salts of certain alpha-arylpropionic acids by reaction with carbon monoxide, at substantially ambient temperature and pressure conditions, of the corresponding arylethyl secondary halide in an anhydrous alcoholic solvent in the presence of alkaline hydroxides and, as catalyst, a salt of cobalt hydrocarbonyl.

THE INVENTION

In accordance with the present invention, ibuprofen or an ester thereof is prepared by carbonylating a 1-halo-1-(4-isobutylphenyl)ethane with carbon monoxide in a neutral or acidic medium containing at least 1 mol of water or of a $C_1$ to about $C_6$ linear or branched aliphatic alcohol per mol of 1-halo-1-(4-isobutylphenyl)ethane at a temperature of between about 10° C. and about 200° C. and a carbon monoxide pressure of at least about one atmosphere in the presence of (a) a palladium compound in which the palladium has a valence of 0-2 and (b) at least one acid-stable ligand.

The 1-halo-1-(4-isobutylphenyl)ethane which is carbonylated in the practice of this invention may be 1-chloro-1-(4-isobutylphenyl)ethane or 1-bromo-1-(4-isobutylphenyl)ethane, and it may be synthesized by any known technique.

The carbonylation of the 1-halo-1-(4-isobutylphenyl)ethane is conducted at a temperature between about 10° C. and about 200° C. preferably about 50°-150° C., and most preferably about 90°-135° C. Higher temperatures can also be used. It has been found that a small advantage in yield is obtained by gradually increasing the temperature within the preferred ranges during the course of the reaction.

The partial pressure of carbon monoxide in the reaction vessel is at least about 1 atmosphere at ambient temperature (or the temperature at which the vessel is charged). Any higher pressures of carbon monoxide can be used up to the pressure limits of the reaction apparatus. A pressure up to about 4500 psig (about 31 MPa) is convenient in the process. More preferred is a pressure from about 300 to about 3000 psig (about 2 to about 21 MPa) at the reaction temperature, and most preferred is a pressure from about 800 to about 2000 psig (about 5 to about 14 MPa).

The carbonylation is conducted in the presence of at least about one mol of water or of a $C_1$ to about $C_6$ linear or branched aliphatic alcohol per mol of the 1-halo-1-(4-isobutylphenyl)ethane; however an excess is preferred in order to assist in driving the reaction to completion. Although there is no real upper limit to the amount of water or alcohol except that imposed by practicality (e.g. the size of the reaction vessel), an amount up to about 100 mols per mol of 1-halo-1-(4-isobutylphenyl)ethane is useful in the process. Further, controlling the amount of water or alcohol used in the process of this invention is advantageous in terms of producing the highest yields. Therefore an amount from about 5 to about 50 mols of water or of alcohol per mol of the 1-halo-1-(4-isobutylphenyl)ethane is preferred, and an amount from about 8 to about 24 mols of water or alcohol per mol of the 1-halo-1-(4-isobutylphenyl)ethane is most preferred. With the use of water, the product ibuprofen is obtained; with an alcohol, the product is an ester of ibuprofen.

Any alcohol which produces an ester of ibuprofen may be used in the practice of this invention. In a preferred embodiment, the lower aliphatic alcohols, i.e., $C_1$ to $C_6$ linear or branched aliphatic alcohols, are used. Examples of the alcohols to be used in this embodiment include methyl alcohol, ethyl alcohol, n-propyl alcohol, isopropyl alcohol, n-, iso-, sec-, and tert-butyl alcohols, the pentyl alcohols, the hexyl alcohols, etc. Methyl alcohol is highly preferred, and ethyl alcohol is most highly preferred. Other alcohols, glycols, or aromatic hydroxy compounds may also be used.

In a preferred embodiment of this invention, the carbonylation reaction is initiated under neutral conditions, i.e., with no added acid. It can also be performed in the presence of an added acid. When acids are added, such acids include sulfuric acid, phosphoric acid, sulfonic acids, or acetic or halo- substituted acetic acids. A hydrogen halide acid such as hydrochloric or hydrobromic acid is preferred. The hydrogen halide may be added as a gas phase or as a liquid phase (in the form of an alcoholic or aqueous solution); in another preferred embodiment it is added as an aqueous solution. Any aqueous concentrations may be used. Hydrochloric acid is particularly preferred, at a concentration up to about 10%; more highly preferred is a concentration from about 10% to about 30%. The amount of acid added is such as to provide up to about 40 mols of hydrogen ion per mol of 1-halo-1-(4-isobutylphenyl)ethane; more preferred is an amount to provide up to about 10 mols of hydrogen ion per mol of 1-halo-1-(4-isobutylphenyl)ethane; the most preferred amount provides up to about 4 mols of hydrogen ion per mol of 1-halo-1-(4-isobutylphenyl)ethane.

The carbonylation process of this invention is conducted in the presence of a reaction-promoting quantity of (a) a palladium compound in which the palladium has a valence of 0–2 and (b) at least one acid-stable ligand. Ligands which may be used include monodentate or multidentate electron-donating substances such as those containing elements P, N, 0, and the like, and those containing multiple bonds such as olefinic compounds. Examples of such acid-stable ligands are trihydrocarbylphosphines, including trialkyl- and triarylphosphines, such as tri-n-butyl-, tricyclohexyl-, and triphenylphosphine; lower alkyl and aryl nitriles, such as benzonitrile and n-propionitrile; ligands containing pi-electrons, such as an allyl compound or 1,5-cyclooctadiene; piperidine, piperazine, trichlorostannate(II), and acetylacetonate; and the like. In one embodiment, the palladium and ligand are added as a pre-formed complex of palladium, such as bis(triphenylphosphine)-palladium-(II) chloride or bromide, tetrakis(triphenylphosphine)-palladium(0), or any other similar complex. In a preferred embodiment, active catalytic species are formed in situ by the addition to the reaction mixture of the individual components, i.e., a ligand and a palladium compound such as palladium(II) chloride, bromide, nitrate, sulfate, or acetate. In the most preferred embodiment, triphenylphosphine and palladium(II) chloride are used and are added individually or together, either simultaneously or sequentially.

The amount of palladium preferably employed is such as to provide from about 4 to about 8000 mols of 1-halo-1-(4-isobutylphenyl)ethane per mol of palladium; more preferred is an amount to provide from about 100 to about 4000 mols of 1-halo-1-(4-isobutYlphenyl)ethane per mol of palladium; the most preferred amount provides from about 200 to 2000 mols of 1-halo-1-(4-isobutylphenyl)ethane per mol of palladium. The process of this invention is conducted in the presence of at least one mol of ligand per mol of palladium. More preferably about 2 to about 40 mols of ligand per mol of palladium are present, and most preferably about 4 to about 20 mols of ligand per mol of palladium are used. Even more highly preferred is an amount from about 8 to about 12 mols of ligand per mol of palladium.

The presence of a solvent is not required in the process of this invention, although it may be desirable in some circumstances. Those solvents which can be used include one or more of the following: ketones, for example, acetone, methyl ethyl ketone, diethyl ketone, methyl-n-propyl ketone, acetophenone, and the like; linear, poly and cyclic ethers, for example, diethyl ether, di-n-propyl ether, di-n-butyl ether, ethyl-n-propyl ether, glyme (the dimethyl ether of ethylene glycol), diglyme (the dimethyl ether of diethylene glycol), tetrahydrofuran, dioxane, 1,3-dioxolane, and similar compounds; and aromatic hydrocarbons, for example, toluene, ethyl benzene, xylenes, and similar compounds. Alcohols are also suitable as solvents, for example, methanol, ethanol, 1-propanol, 2-propanol, isomers of butanol, isomers of pentanol, etc. Acids and esters may also be used, such as formic or acetic acid or ethyl acetate, etc. When an ester or an alcohol is used as solvent, the product is either the corresponding ester of ibuprofen (if no water is present in the reaction) or a mixture of the ester and the ibuprofen itself (if water is present). Most highly preferred are ketones, especially acetone and methyl ethyl ketone. When solvents are used, the amount can be up to about 100 mL per gram of 1-halo-1(4-isobutylphenyl)ethane, but the process is most advantageously conducted in the presence of about 1 to 10 mL per gram of 1-halo-1-(4-isobutylphenyl)ethane.

In those embodiments of this invention in which an ester of ibuprofen is produced, the ester is converted to the acid by conventional methods of hydrolysis.

The following examples are given to illustrate the process of this invention and are not intended as a limitation thereof.

EXAMPLE 1

A 100 mL autoclave was charged with 7.54 g of 1-chloro-1-(4-isobutylphenyl)ethane (CEBB, 97.7%, 37.5 mmol), 1.12 g of a solution of 1.17 weight percent palladium(II chloride in 10% aqueous hydrochloric acid (0.0739 mmol of Pd), 0.224 g of triphenylphosphine (0.854 mmol), 21 mL of methyl ethyl ketone, and 19 g of 10% (by weight) aqueous hydrochloric acid. The resulting mixture was heated under 800 psig carbon monoxide for one hour at 100° C. and one hour at 110 C. The reaction mixture was concentrated in vacuo to remove solvent and was extracted with ether. The ether extract contained 82% yield of ibuprofen by internal standard GC analysis.

EXAMPLE 2

A 300 mL autoclave was charged with 0.66 g of a solution of 1.18 wt. % $PdCl_2$ in 9.6% aqueous hydrochloric acid (0.044 mmol of $PdCl_2$), 0.11 g of triphenylphosphine (0.42 mmol), 5 mL of methyl ethyl ketone, and 25 g of 10% aqueous hydrochloric acid. The autoclave was pressurized to 880 psig with carbon monoxide and the mixture was heated to 110°–120° C. for 20 minutes. Then a solution of 10.6 g of CEBB (92.6%, 49.9 mmol) and 20 mL of methyl ethyl ketone was pumped into the autoclave over about 5 minutes. The mixture was heated at 125 C under 1190 psig carbon monoxide for 2 hours. The organic phase was separated and the aqueous phase was extracted with 10 mL of toluene. The combined organics contained 92% yield of ibuprofen by GC analysis.

EXAMPLE 3

A 300 mL autoclave was charged with 0.11 g of triphenylphosphine (0.42 mmol), 2.0 g of a mixture of 0.39 wt. % $PdCl_2$ in water (0.044 mmol of $PdCl_2$), 10.0 g of CEBB (94.9%, 48.2 mmol), 10 g of water, and 25 mL of methyl ethyl ketone. No HCl was used. The reactor was pressurized to 1430 psig with carbon monoxide then was heated to 125°° C. and was held at that temperature for 1.5 hours under 1800 psig carbon monoxide. The yield of ibuprofen was 94%.

EXAMPLE 4

An autoclave was charged with 0.42 mmol of triphenyl phosphine, 0.66 g of a solution of 1.18 wt.% $PdCl_2$ in 9.6% hydrochloric acid (0.044 mmol of $PdCl_2$), 10 g of water, and 10 mL of methyl ethyl ketone. The autoclave was pressurized to 690 psig with carbon monoxide and heated to 115°–120° C. for about 40 minutes, after which a solution of 9.95 g of CEBB (98.7%, 49.9 mmol) and 15 mL of methyl ethyl ketone was fed to the reactor over 6 minutes. The mixture was heated at 125° C. for 1 hour under about 1450 psig carbon monoxide . The yield of ibuprofen was 92%.

EXAMPLE 5

A 300 mL autoclave was charged with 100 mmol of CEBB (19.9 g of 98.7% CEBB), about 0.10 mmol of recycled Pd catalyst, 1.15 mmol of triphenylphosphine, 5 g of recycled aqueous solution, and 20 mL of water (equivalent to about 25 mL of 10% hydrochloric acid). No solvent was used. The autoclave was pressurized to 950 psig with carbon monoxide and the mixture was heated from 110° to 125° C. over 3 hours to give 78% yield of ibuprofen.

It is obvious that many variations may be made in the products and processes set forth above without departing from the spirit and scope of this invention.

What is claimed is:

1. A process for preparing ibuprofen or an ester thereof which comprises carbonylating a 1-halo-1-(4-isobutylphenyl)ethane with carbon monoxide in a neutral or acidic medium containing at least about 1 mol of water or of a $C_1$ to about $C_6$ linear or branched aliphatic alcohol per mol of 1-halo-1-(4-isobutylphenyl)ethane at a temperature between about 10° C. and about 200° C. and a carbon monoxide pressure of at least about one atmosphere in the presence of (a) a palladium compound in which the palladium has a valence of 0–2 and (b) at least one acid-stable ligand.

2. A process of claim 1 wherein the 1-halo-1-(4-isobutylphenyl)ethane is 1-chloro-1-(4-isobutylphenyl)ethane.

3. A process of claim 1 wherein the 1-halo-1-(4-isobutYlphenyl)ethane is 1-bromo-1-(4-isobutylphenyl)ethane.

4. A process of claim 1 wherein the palladium compound is a palladium(II) compound.

5. A process of claim 4 wherein the palladium compound is palladium(II) chloride.

6. A process of claim 4 wherein the palladium compound is palladium(II) bromide.

7. A process of claim 1 wherein the ligand is a monodentate phosphine ligand.

8. A process of claim 1 wherein the ligand is a tri(hydrocarbyl)phosphine.

9. A process of claim 8 wherein the ligand is triphenylphosphine.

10. A process of claim 1 wherein the palladium compound is bis(triphenylphosphine)palladium(II) chloride or bromide.

11. A process of claim 1 wherein the amount of palladium compound employed is such as to provide about 4–8000 mols of 1-halo-1-(4-isobutylphenyl)ethane per mol of palladium.

12. A process of claim 1 wherein the palladium compound and ligand are employed in amounts such as to provide about 4–20 mols of ligand per mol of palladium in the reaction mixture.

13. A process of claim 1 wherein the palladium compound and ligand are employed in amounts such as to provide about 8–12 mols of ligand per mol of palladium in the reaction mixture.

14. A process of claim 1 wherein the carbonylation is conducted in the presence of water.

15. A process of claim 1 wherein the carbonylation is conducted in the presence of water and no added acid.

16. A process of claim 14 wherein the carbonylation is conducted in the presence of from about 5 to about 50 mols of water per mol of 1-halo-1-(4-isobutylphenyl)ethane.

17. A process of claim 14 wherein the carbonylation is conducted in the presence of from about 8 to about 24 mols of water per mol of 1-halo-1-(4-isobutylphenyl)ethane.

18. A process of claim 1 wherein the carbonylation is conducted in the presence of from about 8 to about 24 mols of ethanol per mol of 1-halo-1-(4-isobutylphenyl)ethane.

19. A process of claim 1 wherein the carbonylation is conducted in the presence of added hydrogen halide.

20. A process of claim 19 wherein the hydrogen halide is hydrogen chloride.

21. A process of claim 19 wherein the hydrogen halide is hydrogen bromide.

22. A process of claim 19 wherein the hydrogen halide is added as an aqueous solution.

23. A process of claim 22 wherein the hydrogen halide is hydrogen chloride and the concentration of the aqueous solution is a concentration up to about 30% (by weight) hydrogen chloride.

24. A process of claim 22 wherein the hydrogen halide is hydrogen chloride and the concentration of the aqueous solution is a concentration up to about 10% (by weight) hydrogen chloride.

25. A process of claim 19 wherein the amount of hydrogen halide added is an amount up to about 40 mols per mol of 1-halo-1-(4-isobutylphenyl)ethane.

26. A process of claim 1 wherein the carbonylation is conducted in a solvent.

27. A process of claim 26 wherein the solvent is a ketone.

28. A process of claim 27 wherein the solvent is acetone.

29. A process of claim 27 wherein the solvent is methyl ethyl ketone.

30. A process of claim 1 wherein the temperature is in the range of about 50°–150° C.

31. A process of claim 1 wherein the temperature is in the range of about 90°–135° C.

32. A process of claim 30 wherein the temperature is gradually increased during the reaction.

33. A process of claim 1 wherein the carbon monoxide pressure is in the range of about 300–3000 psig.

34. A process of claim 1 wherein the carbon monoxide pressure is in the range of about 800–2000 psig.

35. A process for preparing ibuprofen which comprises carbonylating 1-chloro-1-(4-isobutylphenyl)ethane with carbon monoxide in an acidic medium containing methyl ethyl ketone as a solvent and about 8–24 mols of water per mol of 1-chloro-1-(4-isobutylphenyl)ethane at a temperature in the range of about 50°–150° C. and a carbon monoxide pressure in the range of about 800–2000 psig in the presence of (a) a palladium(II) compound and (b) at least one acid-stable monodentate phosphine ligand and in the presence of an amount of hydrogen chloride such as to provide an amount up to about 10 mols of hydrogen chloride per mol of 1chloro-1-(4-isobutylphenyl)ethane 36. A process of claim 35 wherein the palladium (II) compound is palladium (II) chloride and the ligand is triphenylphosphine.

37. A process of claim 35 wherein the palladium and the ligand are present in amounts such as to provide about 200–2000 mols of 1-chloro-1-(4-isobutylphenyl)ethane per mol of palladium and about 4–20 mols of ligand per mol of palladium.

38. A process of claim 35 wherein the hydrogen chloride is added as an aqueous solution with a concentration from about (by weight) to about 30% (by weight) HCl.

39. A process for preparing ibuprofen which comprises carbonylating 1-chloro-1-(4-isobutylphenyl)ethane with carbon monoxide in a neutral or acidic medium containing methyl ethyl ketone as a solvent and about 8-24 mols of water per mol of 1-chloro-1-(4-isobutylphenyl)ethane and no added acid at a temperature in the range of about 50°-150° C. and a carbon monoxide pressure in the range of about 800-2000 psig (about 5-14 MPa), in the presence of (a) a palladium(II) compound and (b) at least one acid-stable monodentate phosphine ligand.

40. A process of claim 39 wherein the palladium (II) compound is palladium (II) chloride and the ligand is triphenylphosphine.

41. A process of claim 39 wherein the palladium and the ligand are present in amounts such as to provide about 200-2000 mols of 1-chloro-1-(4-isobutylphenyl)ethane per mol of palladium and about 4-20 mols of ligand per mol of palladium.

* * * * *

UNITED STATES PATENT AND TRADEMARK OFFICE
CERTIFICATE OF CORRECTION

PATENT NO.  : 4,990,658

DATED       : February 5, 1991

INVENTOR(S) : Barbara C. Stahly, et al.

It is certified that error appears in the above-identified patent and that said Letters Patent is hereby corrected as shown below:

Column 6, line 58, reads "1chloro" and should read -- 1-chloro --.

Column 7, line 1, reads "about (by weight)" and should read -- about 10% (by weight) --.

Signed and Sealed this

Fifteenth Day of September, 1992

Attest:

DOUGLAS B. COMER

Attesting Officer   Acting Commissioner of Patents and Trademarks

UNITED STATES PATENT AND TRADEMARK OFFICE
CERTIFICATE OF CORRECTION

PATENT NO. : B1-4,990,658  
DATED : February 5, 1991  
INVENTOR(S) : Barbara C. Stahly, et al Page 1 of 2

It is certified that error appears in the above-indentified patent and that said Letters Patent is hereby corrected as shown below:

On the title page, item [56], of the Reexamination Certificate should read

References Cited

U.S. Patent Documents

| | | |
|---|---|---|
| 3,928,429 | 12/1975 | El-Chahawi et al. |
| 4,543,217 | 9/1985 | Erpenbach et al. |

Foreign Patent Documents

| | | |
|---|---|---|
| 59-95238 | 6/1984 | Japan |
| 59-95239 | 6/1984 | Japan |
| 56-35659 | 8/1981 | Japan |
| 338852 | 10/89 | European Patent Office |

UNITED STATES PATENT AND TRADEMARK OFFICE
CERTIFICATE OF CORRECTION

PATENT NO. : B1-4,990,658
DATED : February 5, 1991
INVENTOR(S) : Barbara C. Stahly, et al It is certified that error appears in the above-indentified patent and that said Letters Patent is hereby corrected as shown below:

Other Publications

March, *Advanced Organic Chemistry*, Second Edition, McGraw-Hill Book Company, New York, pp. 392-394 (1977).

Signed and Sealed this

Twelfth Day of March, 1996

*Attest:*

BRUCE LEHMAN

*Attesting Officer*     Commissioner of Patents and Trademarks

REEXAMINATION CERTIFICATE (2368th)

United States Patent [19]

Stahly et al.

[11] B1 4,990,658

[45] Certificate Issued  Aug. 30, 1994

[54] PROCESS FOR PREPARING IBUPROFEN AND ITS ALKYL ESTERS

[75] Inventors: Barbara C. Stahly; Ronny W. Lin, both of Baton Rouge; E. E. Atkinson, Jr., Greenwell Springs, all of La.

[73] Assignee: Ethyl Corporation, Richmond, Va.

Reexamination Request:
No. 90/002,654, Feb. 28, 1992

Reexamination Certificate for:
Patent No.: 4,990,658
Issued: Feb. 5, 1991
Appl. No.: 451,563
Filed: Dec. 18, 1989

Certificate of correction issued Feb. 5, 1991.

[51] Int. Cl.$^5$ .................................... C07C 51/14
[52] U.S. Cl. .................................... 562/406; 560/105

[58] Field of Search .................. 562/416; 560/105

[56] References Cited

U.S. PATENT DOCUMENTS 3,928,429  12/1975  El-Chahawi et al. .
4,543,217   9/1985  Erpenbach .

Primary Examiner—Alan L. Rotman

[57] ABSTRACT

A new process for preparing ibuprofen or its alkyl esters is provided. A 1-halo-1-(4-isobutylphenyl)ethane is reacted with carbon monoxide is the presence of water or an alcohol at a temperature between about 10° C. and about 200° C. An excess of several moles of water or alcohol is preferred. An acid such as hydrochloric acid may also be added. As catalyst, a palladium compound and at least one-stable ligand are present; however an excess of ligand over palladium is advantageous.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-41 is confirmed.

* * * * *